(12) United States Patent
Allen et al.

(10) Patent No.: US 6,768,629 B1
(45) Date of Patent: Jul. 27, 2004

(54) MULTIPIN FEEDTHROUGH CONTAINING A GROUND PIN PASSING THROUGH AN INSULATOR AND DIRECTLY BRAZED TO A FERRULE

(75) Inventors: Kevin M. Allen, Eldersburg, MD (US); Thomas W. Shipman, Columbia, MD (US); Christine Frysz, Columbia, MD (US)

(73) Assignee: Greatbatch-Hittman, Inc., Columbia, MD (US)

( * ) Notice: Subject to any disclaimer, the term of this patent is extended or adjusted under 35 U.S.C. 154(b) by 0 days.

(21) Appl. No.: 10/452,704

(22) Filed: Jun. 2, 2003

(51) Int. Cl.[7] ............................. H01G 4/35; H01G 4/00
(52) U.S. Cl. ...................................... 361/302; 29/25.42
(58) Field of Search ............................. 361/302, 306.1; 174/152 GM, 50.61; 607/36–37, 9; 29/25.42

(56) References Cited

U.S. PATENT DOCUMENTS

| | | | |
|---|---|---|---|
| 4,225,262 A | * | 9/1980 | Koop et al. .................. 403/272 |
| 4,547,624 A | | 10/1985 | Tower et al. |
| 5,103,818 A | | 4/1992 | Masten et al. |
| 5,104,755 A | | 4/1992 | Taylor et al. |
| 5,306,581 A | | 4/1994 | Taylor et al. |
| 5,406,444 A | | 4/1995 | Selfried et al. |
| 5,817,984 A | | 10/1998 | Taylor et al. |
| 5,836,992 A | | 11/1998 | Thompson et al. |
| 5,851,222 A | | 12/1998 | Taylor et al. |
| 5,866,851 A | | 2/1999 | Taylor et al. |
| 5,871,513 A | | 2/1999 | Taylor et al. |
| 5,905,627 A | | 5/1999 | Brendel et al. |
| 6,076,017 A | | 6/2000 | Taylor et al. |
| 6,275,369 B1 | | 8/2001 | Stevenson et al. |
| 6,321,114 B1 | | 11/2001 | Nutzman et al. |
| 6,490,148 B1 | | 12/2002 | Allen et al. |
| 2001/0050837 A1 | | 12/2001 | Stevenson et al. |

* cited by examiner

Primary Examiner—Chau N. Nguyen
Assistant Examiner—Eric Thomas
(74) Attorney, Agent, or Firm—Michael F. Scalise

(57) ABSTRACT

A filtered feedthrough including a ferrule surrounding an insulator supporting one or more lead wires and at least one ground pin is described. The insulator defines a channel cutout extending from a first insulator side to a channel cutout bottom part way through the thickness of the insulator and in communication with the ferrule. An attached filter capacitor shunts electromagnetic interference from the lead wire to the ground pin, and the ground pin is in electrical communication with the ferrule by way of a ferrule-ground pin braze joint formed in the channel cutout.

35 Claims, 2 Drawing Sheets

MULTIPIN FEEDTHROUGH CONTAINING A GROUND PIN PASSING THROUGH AN INSULATOR AND DIRECTLY BRAZED TO A FERRULE

BACKGROUND OF THE INVENTION

1. Field of the Invention

The present invention generally relates to feedthroughs that provide electrical paths for implantable medical devices. The feedthroughs hermetically connect the components, including the electrical power and control circuitry, housed inside the casing of an implantable medical device with the conductors delivering the therapy to the body being assisted. More particularly, the present invention helps prevent electromagnetic interference (hereinafter EMI) with critical electrical signals in these devices.

2. Prior Art

Medical devices, including implantable cardiac pacemakers and implantable cardiac defibrillators currently in use for correcting cardiac abnormalities, are adversely affected by spurious EMI. Spurious EMI is highly undesirable because it can interfere with proper functioning of the implanted medical device, either, by inhibiting a proper response or by causing an improper one, and can otherwise cause the device to unpredictably malfunction. Spurious EMI signals are emitted from such common sources as television transmitters, cell phones, cell towers, and anti-theft detection devices. Thus, all of these EMI emitters can cause significant problems for individuals with implantable medical devices.

The structure of a pacemaker or a defibrillator device typically includes a casing as a housing for a pulse generator and associated circuitry, and a battery that serves as a power supply. One or more conductive lead wires extend from the pulse generator circuit in the interior of the device and pass through the casing where they connect via a medical lead to an electrode surgically attached to an appropriate location in the heart. A feedthrough allows the lead wires to hermetically pass from the interior of the device, through the casing and but to the medical lead connected to the heart. The typical feedthrough comprises a ferrule mountable on the device casing with an insulator positioned within the ferrule. The lead wires pass through the insulator from the interior of the device to the exterior in a non-conductive manner. This is possible because the lead wires are electrically isolated from the metallic device casing.

Shunting the lead wires to a ground wire or pin by a filter capacitor connected between them essentially eliminates stray EMI. There may be more than one ground wire. Typically, one capacitor is positioned between each lead wire and at least one of the ground pins. When used with a multipin feedthrough, these capacitors are often built as a monolithic structure or array and are referred to as an internally grounded feedthrough. If the array is in the form of a right circular cylinder, it is designated a discoidal capacitor.

However, prior art feedthrough devices are not without problems. For example, if the internally grounded feedthrough is to effectively filter EMI, the ground pin or pins must be electrically connected to the ferrule. Spot welding or brazing the ground pin or pins to the ferrule typically accomplishes this. Spot welding and brazing are time consuming, increase the number of components required, increase the number of manufacturing steps, and result in a ground that is not centrally located.

Another method for grounding the feedthrough is to braze a metallic member to one wire passing through a hole in the ceramic insulator. The opposite end of the metallic member is then brazed to an insulator-ferrule braze joint. Problems associated with this construction include undesirably increasing the number of components necessary for the feedthrough, increasing the need for complicated manufacturing processes to accomplish the required brazing, and decreasing production yields.

Yet another past attempt at grounding a feedthrough is to furnish the insulator with a metallized ground strip down its side. Gold is then flowed down the ground strip to the insulator-ferrule braze joint. This design presents significant fixturing problems, has high variability, and often results in a very thin gold strip with excessive resistivity, thus making it unsuitable for many implantable device applications.

Additionally, ground members that are brazed directly to the ferrule can develop hermetic failures after completion of device assembly if the brazing process is not controlled and dissolution of titanium in the gold braze is excessive. Braze failures occur when the titanium to gold ratio is too high. This causes brittleness in areas of the braze fillet when the lead wire is subjected to bending strain or thermal stresses.

Then, there are feedthroughs that centralize the ground pin or pins where they are directly attached to the ferrule. However, these designs require multiple insulators, multiple components, increased seal lengths, increased feedthrough size, increased production time, and, ultimately, increased expense.

Thus, there is a need for an internally grounded feedthrough, preferably filtered, that comprises at least one centralized ground wire or pin with minimal spacing between the at least one lead wire and the at least one ground pin. The feedthrough needs to have a high degree of durability and be of a highly manufacturable design with a minimal number of components. This helps lower production costs and susceptibility to process variations while retaining ductile braze bonds.

SUMMARY OF THE INVENTION

The present multipin feedthrough comprises a ferrule surrounding an insulator supporting one or more lead wires and at least one ground pin. The insulator defines a channel cutout extending from a first insulator side to a channel cutout bottom part way through the thickness of the insulator and in communication with the ferrule. An attached filter capacitor shunts electromagnetic interference from the lead wire to the ground pin, and the ground pin is in electrical communication with the ferrule by way of a ferrule-ground pin braze joint formed in the channel cutout. This structure overcomes problems associated with prior art filter feedthroughs by shunting undesirable EMI directly from the ground pin to the ferrule along the ferrule-ground pin braze joint.

DETAILED DESCRIPTION OF THE PREFERRED EMBODIMENTS

Figure 1:
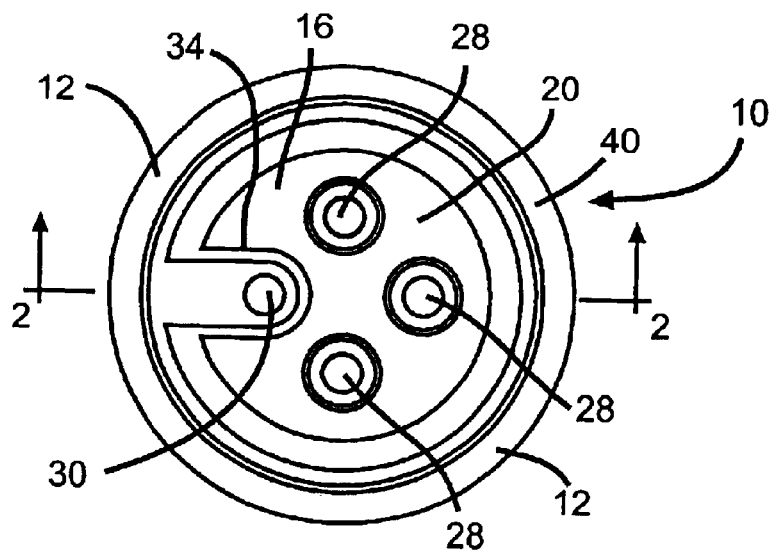
FIG. 1 is top plan view of the multipin feedthrough of the present invention.
Figure 2:
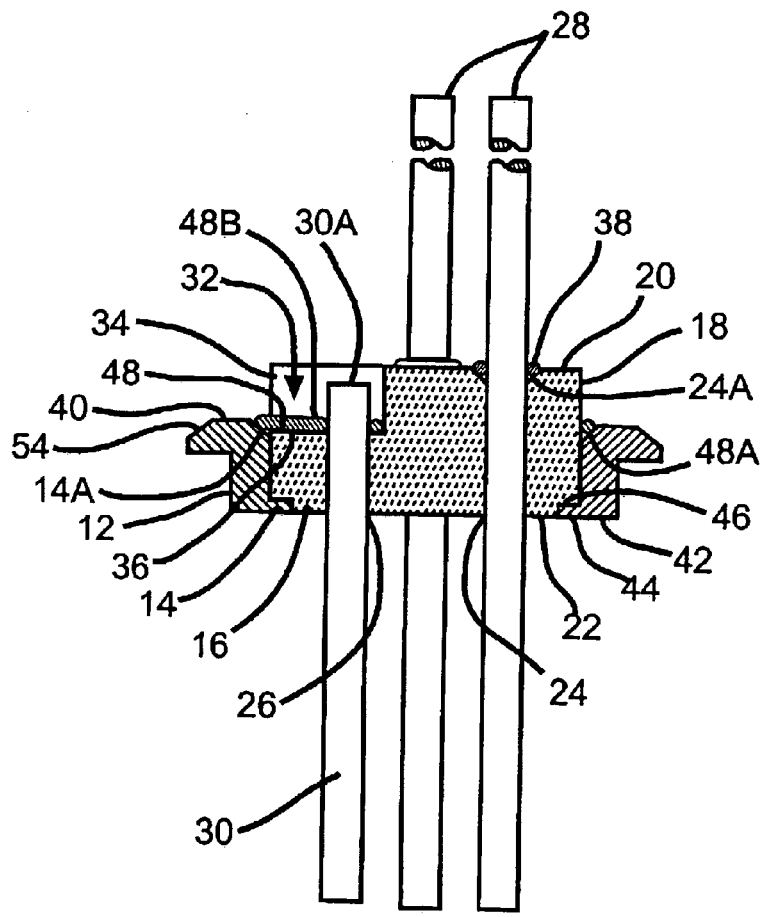
FIG. 2 is a cross sectional view taken along line 2—2 of FIG. 1.
Figure 3:
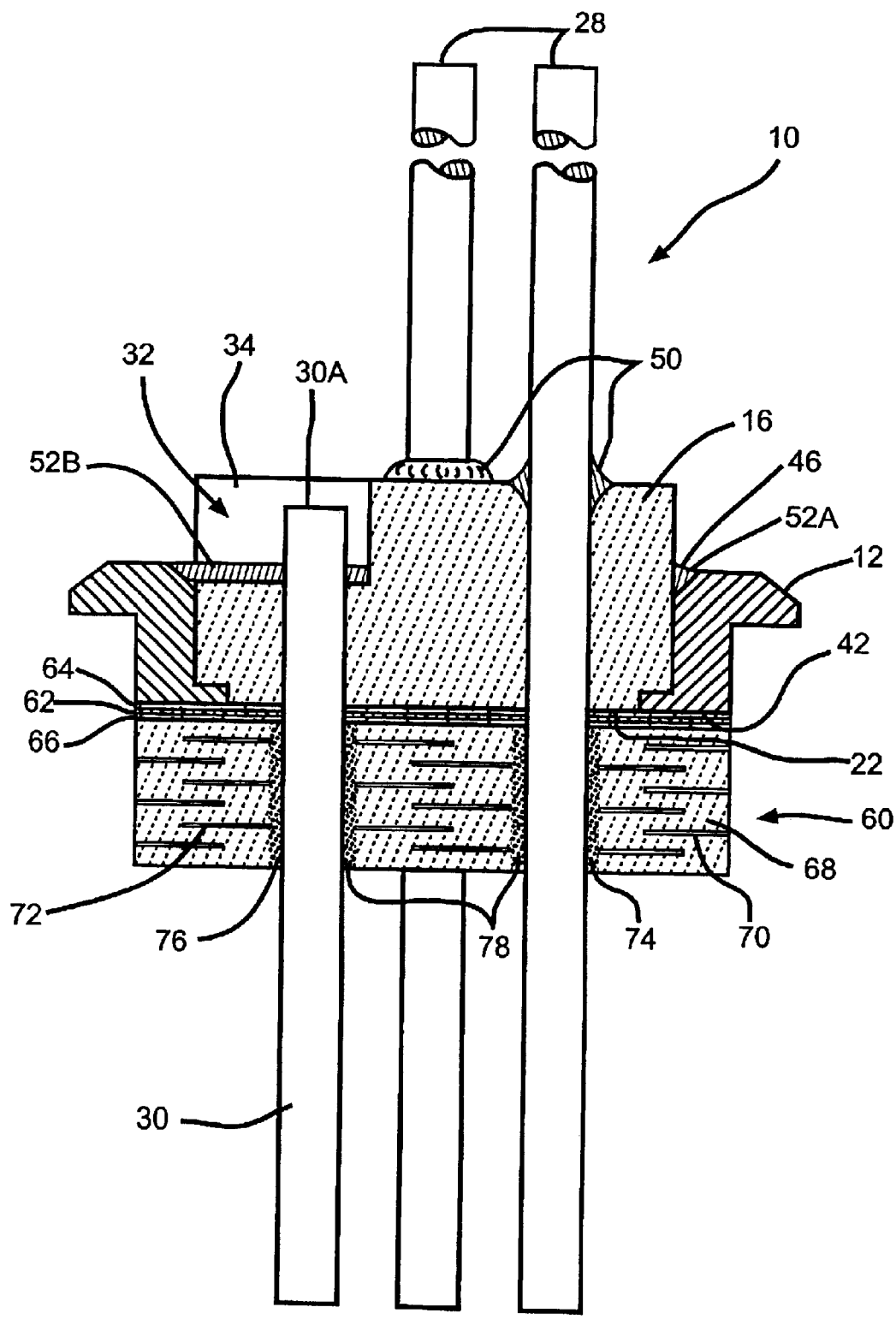
FIG. 3 is a cross sectional view of the multipin feedthrough shown in FIG. 1 and with an attached filter capacitor.

As shown in FIGS. 1 to 3, the internally grounded feedthrough 10 of the present invention comprises a ferrule 12 defining an insulator-receiving bore 14 surrounding an insulator 16. The ferrule 12 is of an electrically conductive material such as titanium. The insulator 16 is of a ceramic material such as of alumina, which is highly purified aluminum oxide, and comprises a sidewall 18 extending to a first upper side 20 and a second lower side 22. The insulator 16 has one or more lead bores 24 and at least one ground bore 26 (FIG. 2). Lead wires 28 are received in the lead bores 24 while a ground pin 30 is received in the ground bore 26.

As shown in the sectional views of FIGS. 2 and 3, the insulator 16 further defines a channel cutout 32 in the shape of an inlet extending from the upper wall 20 part way through the thickness of the side wall 18 at the ground bore 26. In that manner, the channel cutout 32 comprises a substantially U-shaped sidewall 34 extending from the upper wall 20 to a channel bottom wall 36 and the sidewall 18.

As shown in FIG. 2, the lead bores 24 each include an annular bevel 24A at the upper wall 20. To assemble the feedthrough, O-ring shaped conductive preforms are 38 positioned in the annular bevels 24A, surrounding the lead wires 28 extending through the bores. The insulator-receiving bore 14 of the ferrule 12 is likewise provided with an annual bevel 14A at an upper ferrule sidewall 40. A lower ferrule side 42 includes a protruding inner lip 44 fitted in an edge cutout 46 when the insulator 16 is received in the bore 14 of the ferrule 12.

The plane of the channel bottom wall 36 is horizontally aligned approximately with the mid point of the thickness of the bevel 14A. A unitary custom-shaped ground pin/ferrule braze preform 48 comprises an insulator-ferrule portion 48A and a ferrule-ground pin portion 48B. The insulator-ferrule portion 48A fits around the insulator 16 while the ferrule-ground pin portion 48B is received in the channel cutout 32. The ground pin 30 extends through the insulator ground bore 26 with its upper end 30A terminating between the upper wall 20 and the channel cutout bottom wall 36. The thusly-assembled feedthrough assembly is then heated in an oven or furnace to melt the preforms 38, 48 and cause them to form their respective braze structures 50 and 52A, 52B (FIG. 3).

The insulator-ferrule braze joint 52A and the ferrule-ground pin braze joint 52B correspond to the ferrule-insulator portion 48A and the ferrule-ground pin portion 48B of the preform 48, respectively. The ferrule-ground pin braze joint 52B resides in the channel cutout 32 and provides a direct, low resistance electrical path from the ground pin 30 to the ferrule 12.

In the embodiment of the present invention illustrated in FIGS. 1 to 3, the channel cutout bottom 36 is spaced elevationally below the lower edge of the annular bevel 14A of the insulator-receiving bore 14 with the insulator 16 received in the ferrule 12. In other embodiments, the channel cutout bottom 36 may be flush with or substantially flush with the upper ferrule sidewall 40 when the insulator 16 is received in the ferrule 12. In yet other embodiments, the channel cutout bottom 36 may be slightly elevated relative to the adjacent second ferrule sidewall 40. In that respect, the position of the channel cutout bottom 36 preferably ranges from about 0.002 inches above or below the bevel 14A.

While the channel cutout 32 is shown as being substantially U-shaped, that is not necessary. In other embodiments, the channel cutout in the insulator 16 may be circular, angular, polygonal, and combinations thereof. In any event, the channel forms a pathway from the ground pin 30 to the ferrule 12 with the unitary ground pin/ferrule preform 48 shaped accordingly. It is also noted that the cross section of the insulator 16 may be other than circular. It could, for example, be oval shaped, rectangular, or elliptical.

The O-ring-shaped braze preforms 38 and the unitary ground pin/ferrule preform 48 may comprise gold and gold alloys. They may also comprise any suitable biocompatible material. Then, if the feedthrough 10 is used where it will contact bodily fluids, the resulting brazes do not need to be covered with a biocompatible coating material.

In other embodiments, if the brazes are not biocompatible, they are coated with a layer/coating of biocompatible/biostable material. Broadly, the biocompatibility requirement is met if contact of the braze/coating with body tissue and blood results in little or no immune response from the body, especially thrombogenicity (clotting) and encapsulation of the electrode with fibrotic tissue. The biostability requirement means that the braze/coating remains physically, electrically, and chemically constant and unchanged over the life of the patient.

This layer/coating may be deposited by sputtering electrolysis, and other methods. The coating may comprise gold, gold alloys, niobium, carbon, platinum, and titanium nitrides, and combinations thereof. The coating must be pinhole free so that the underlying braze does not contact body fluids. This allows the use of non-biocompatible brazes for the preforms 38, 48, which are less expensive than solid gold preforms.

The most critical property in a medical implant feedthrough design is its ability to remain hermetic throughout device service life. The nature of the braze bonds and their sensitivity to environmental conditions are greatly affected by the device fabrication process (installation by laser welding by the pacemaker manufacturer) and environmental conditions while in service (body fluid is highly corrosive). For the braze connecting from the ground pin to the ferrule of a feedthrough by way of the present channel cutout 32 in the ceramic insulator 16, the bond to the ferrule as well as to the ceramic material needs to deform in a ductile manner when subsequent assembly conditions create stresses (e.g., heating and cooling cycles that develop during welding or bending the ground pin to facilitate electronics attachment).

Typically, ferrule and braze materials, as well as metallization and braze material combinations, form alloys that solidify as intermetallics. These intermetallics often show only modest ductility prior to failure. If material combinations are not judiciously selected and processes not understood and controlled, significant dissolution can occur and result in brittle fracture of the bond. Of particular concern are failures that occur in a latent mode resulting in compromised hermetic integrity, potentially after implantation.

Accordingly, a unique challenge for connecting the ground pin 30 to the ferrule 12 of the present invention is that the braze material residing in the channel cutout 32 must form an integral part of the hermetic seal joint. This requires the present uniquely designed gold braze material preform 48. In conventional human implant hermetic feedthroughs, whether they are of a filtered or unfiltered type, the volume of braze material is, by design, relatively small. Additionally, ground pins are metal to metal brazed directly to the ferrule without benefit of a connecting channel for the braze. Hermetic failures can occur, particularly if braze material processing is not controlled and dissolution of titanium in the gold braze is excessive, resulting in a significant amount of weak brittle intermettalic developing.

In the present invention, isolation of the ground pin 30 from the ferrule 12 eliminates such metal-to-metal bonds and, therefore, minimizes any opportunity for excessively brittle intermetallic formation. However, the relatively large volume of specially shaped braze material residing in the channel cutout 32 means that higher stresses due to shrinkage and mismatches in the thermal coefficient of expansion (TCE) of the braze material become a major design challenge. The biggest concern is the added stress,in tension or shear transmitted to the metallic braze layer hermetically sealing between the ground pin, insulator and ferrule. This layer allows the braze material to wet the alumina material of the insulator and form the hermetic seal, and is preferably applied by sputtering or equivalent methods.

In order to overcome problems associated with mismatching the TCE of high alumina content ceramic insulator with the TCE of typically used noble metal braze materials, a unique metallization process is required. The metallization process preserves system malleability and encourages retention of adhesion strength to the alumina ceramic insulator 16 while allowing for good wetting of the braze material. This is preferably accomplished through a layered structure of titanium coated with molybdenum on the alumina ceramic insulator. Titanium is the active layer and molybdenum is the barrier layer controlling how much titanium can actually dissolve in the gold. For example, 2 to 4 microns of titanium are sputtered on the ceramic surface followed by 2 to 4 microns of molybdenum. Actual thicknesses are dependent on the design, brazing process parameters, application technique; and subsequent potential environmental exposures.

In that regard, the titanium layer provides the interaction with the glass phases and alumina particle matrix of the ceramic insulator 16 to create a hermetic bond. The molybdenum layer protects the titanium layer from excessive oxidation prior to brazing and acts as a barrier between the gold braze material and the titanium layer. Without the molybdenum barrier layer, an excessive exposure of the titanium layer to the molten gold would accelerate the inherent alloying process and eventually lead to de-wetting, then hermetic failure.

Therefore, the titanium/molybdenum metallization structure in concert with the gold braze preforms 38, 42 not only provides a sound hermetic bond, it is also sufficiently ductile to facilitate secondary device assembly without compromising hermeticity. This, in turn, prevents the development of fractures from environmental conditions while the device is in service.

In addition to titanium and molybdenum, other noble materials useful with a gold braze include, but are not limited to, niobium, carbon, carbon nitride, platinum, titanium nitrides, titanium carbide, palladium, iridium,iridium oxide, tantalum, tantalum oxide, ruthenium, ruthenium oxide, zirconium, and mixtures thereof. Parylene, alumina, silicone, fludropolymers, and mixtures thereof are also useful materials for this purpose.

A preferred metallization application method is by sputtering. Other methods include, but are not limited to, chemical vapor deposition, laser or other physical vapor deposition processes, vacuum evaporation, thick film application methods, plating, and aerosol spray deposition.

A surrounding flange 54 extends from the ferrule 12 to facilitate attachment of the feedthrough 10 to the casing (not shown) of, for example, an implantable medical device. These medical devices may include implantable cardiac defibrillators, implantable cardioverter defibrillators, cochlear implants, neurostimulators, internal drug pumps, deep brain stimulators, hearing assist devices, incontinence devices, obesity treatment devices, Parkinson's disease therapy devices, bone growth stimulators, and the like. The method of attachment may be by laser welding or other suitable methods.

As further shown in FIG. 3, a filter chip capacitor 60 for filtering undesirable EMI is preferably joined to the multipin feedthrough 10 contacting the lower insulator side 22 and the lower ferrule side 42. A thermoplastic or ceramic spacer 62 held in place by layers 64 and 66 of a non-conductive adhesive makes this connection. The openings in the spacer through which the lead wires 28 and 30 pass are sized to fit so that conductive material added to the pin gaps 78 does not flow past the interface surface 66 of the capacitor and cause electrical shorting between the other pins or the flange.

The capacitor 60 coupled to the feedthrough 10 provides a filtered feedthrough. The filter capacitor 60 preferably has a circular cross section matching the cross section of the ferrule 12 and comprises a dielectric material 68 with an internal first set of capacitor plates 70 and an internal second set of capacitor plates 72. The capacitor has lead bores 74 into which the lead wires 28 are received, and a ground bore 76 into which the ground pin 30 is received. Then, with the lead wires 28 aligned with the lead bores 74, and the ground pins 30 aligned with the ground bore 76, the capacitor 60 is moved over the ground pin 30 and the lead wires 28 and contacted to the spacer 62 adhered to the lower sides 22, 42 of the insulator 16 and the ferrule 12, respectively. The lead wires 28 are coupled to the first set of electrode plates 70, and the ground pin 30 is coupled to the second set of electrode plates 72. The material 78 used to couple the lead wires 28 and ground pin 30 to the respective first and second sets of electrode plates 70, 72 may comprise solder, silver filled polyamide, and other suitable materials.

Coupling the capacitor 60 with the lead wires 28 and the ground pin 30 results in an electrical path running from the second set of plates 72 to the ground pin 30, along the ferrule-ground pin braze joint 52B in the channel cutout 32, and directly out to the ferrule 12. In this manner the feedthrough 10 shunts spurious EMI signals to ground, thereby protecting the internal circuitry of the medical device. As previously discussed, there may be more than one ground pin. In that case, each ground pin is coupled to a lead wire by a capacitor.

It will be appreciated that various modifications to the inventive concepts described herein may be apparent to those skilled in the art without departing from the scope of the present invention as defined by the hereinafter appended claims.

What is claimed is:

1. A feedthrough, which comprises:
   a) an insulator of electrically non-conductive material having a thickness defined by an insulator side wall extending to and meeting with a first insulator side and a second insulator side, wherein the insulator has at least one lead wire bore extending from the first side to the second side thereof and at least one ground pin bore;
   b) a recess in the insulator extending from the first insulator side part way through the insulator thickness to a recess bottom;
   c) a lead wire received in the lead wire bore, the lead wire having opposed first and second ends disposed spaced from the respective first and second sides of the insulator;
   d) a ground pin received in the ground pin bore, the ground pin having opposed third and fourth ends disposed spaced from the respective recess bottom and the second side of the insulator;

e) a ferrule of an electrically conductive material and comprising a surrounding sidewall extending to a first ferrule side and a second ferrule side, wherein the ferrule sidewall surrounds the insulator supported therein with the recess bottom disposed between the first ferrule side and the second ferrule side; and f) a first braze material hermetically sealing the lead wire to the insulator and a second braze material hermetically sealing the insulator and the ground pin electrically connected to the ferrule by the second,braze material.

2. The feedthrough of claim 1 wherein the insulator includes a bevel where the first braze seals between the lead wire and the insulator.

3. The feedthrough of claim 2 wherein the first braze material seals between the lead wire and the insulator at the first side of the insulator.

4. The feedthrough of claim 1 wherein the second braze material is provided by a unitary braze preform comprising an insulator-ferrule portion and a channel portion, the channel portion received in the recess contacting the recess bottom and extending to and contacting the ground pin and the ferrule side wall to provide a direct electrical path from the ground pin to the ferrule.

5. The feedthrough of claim 1 wherein the ferrule includes a bevel where the second braze seals between the ferrule and the insulator.

6. The feedthrough of claim 1 wherein the third end of the ground pin is disposed between the first side of the insulator and the recess bottom.

7. The feedthrough of claim 1 wherein the first insulator side is spaced above the first ferrule side.

8. The feedthrough of claim 1 wherein the second ferrule side is substantially coplanar with the second insulator side.

9. The feedthrough of claim 1 wherein the first and second braze materials are the same or different.

10. The feedthrough of claim 1 wherein the first and second braze materials comprise a biocompatible/biostable material.

11. The feedthrough of claim 10 wherein the biocompatible/biostable material is of gold or a gold alloy.

12. The feedthrough of claim 1 wherein the first and second braze materials are coated with a pinhole free layer of a biocompatible/biostable material.

13. The feedthrough of claim 12 wherein the biocompatible/biostable material is selected from the group consisting of gold, gold alloys, niobium, carbon, carbon nitride, platinum, titanium, titanium nitrides, titanium carbide, palladium, iridium, iridium oxide, tantalum, tantalum oxide, ruthenium, ruthenium oxide, alumina, zirconium, parylene, silicone, fluoropolymers, and mixtures thereof.

14. The feedthrough of claim 1 wherein the insulator is comprised of alumina.

15. The feedthrough of claim 1 further comprising a filter capacitor in electrical communication with the at least one lead wire and the at least one ground pin, wherein the filter capacitor provides for shunting electromagnetic interference from the lead wire to the ground pin in electrical communication with the ferrule along the second braze.

16. A filtered feedthrough, which comprises:

a) an insulator of electrically non-conductive material having a thickness defined by an insulator side wall extending to and meeting with a first insulator side and a second insulator side, wherein the insulator has at least one lead wire bore extending from the first side to the second side thereof and at least one ground pin bore;

b) a recess in the insulator extending from the first insulator side part way through the insulator thickness to a recess bottom;

c) a lead wire received in the lead wire bore, the lead wire having opposed first and second ends disposed spaced from the respective first and second sides of the insulator;

d) a ground pin received in the ground pin bore, the ground pin having opposed third and fourth ends disposed spaced from the respective recess bottom and the second side of the insulator;

e) a ferrule of an electrically conductive material and comprising a surrounding sidewall extending to a first ferrule side and a second ferrule side, wherein the ferrule sidewall surrounds the insulator supported therein with the recess bottom disposed between the first ferrule side and the second ferrule side;

f) a first braze material hermetically sealing the lead wire to the insulator and a second braze material hermetically sealing the insulator and the ground pin electrically connected to the ferrule by the second braze material; and g) a filter capacitor in electrical communication with the at least one lead wire and the at least one ground pin, wherein the filter capacitor provides for shunting electromagnetic interference from the lead wire to the ground pin in electrical communication with the ferrule along the second braze.

17. The filtered feedthrough of claim 16 wherein the third end of the ground pin is disposed between the first insulator side and the recess bottom with the first insulator side being spaced above the first ferrule side.

18. The filtered feedthrough of claim 16 wherein the second ferrule side is substantially coplanar with the second insulator side and the filter capacitor contacts the ferrule and the insulator at their second sides.

19. The filtered feedthrough of claim 16 wherein the filter capacitor has a first set of electrode plates electrically connected to the ground pin and a second set of electrode plates electrically connected to the lead wire.

20. The filtered feedthrough of claim 16 wherein the ferrule sidewall comprises a protruding inner lip and the insulator sidewall has an edge cutout that receives the protruding inner lip when the insulator is supported by the ferrule sidewall.

21. An insulator for a feedthrough, the insulator of an electrically non-conductive material and comprising:

a) an insulator sidewall defining a thickness extending to and meeting with a first insulator side and a second insulator side;

b) a recess in the insulator extending from the first insulator side part way through the insulator thickness to a recess bottom;

c) at least one lead wire bore extending from the first side to the second side of the insulator; and d) at least one ground pin bore extending from the first insulator side to the recess bottom.

22. The insulator of claim 21 wherein the recess is an inlet extending from the insulator sidewall to the first insulator side and the recess bottom.

23. The insulator of claim 21 including a bevel about the lead wire bore at the first insulator side.

24. A method for providing a feedthrough, comprising the steps of:

a) providing an insulator of electrically non-conductive material having a thickness defined by an insulator sidewall extending to and meeting with a first insulator side and a second insulator side, the insulator provided with at least one lead wire bore extending from the first side to the second side thereof and at least one ground pin bore;

b) forming a recess in the insulator extending from the first insulator side part way through the insulator thickness to a recess bottom;

c) positioning a lead wire in the lead wire bore, the lead wire having opposed first and second ends disposed spaced from the respective first and second sides of the insulator;

d) positioning a ground pin received in the ground pin bore, the ground pin having opposed third and fourth ends disposed spaced from the respective recess bottom and the second side of the insulator;

e) providing a ferrule of an electrically conductive material comprising a surrounding sidewall extending to a first ferrule side and a second ferrule side;

f) supporting the insulator inside the surrounding ferrule sidewall with the recess bottom disposed between the first ferrule side and the second ferrule side;

g) brazing a first material sealing between the lead wire and the insulator; and h) brazing a second material sealing between the insulator and the ground pin electrically connected to the ferrule.

25. The method of claim 24 including providing the insulator with a bevel where the first braze seals between the lead wire and the insulator.

26. The method of claim 24 including providing the second braze material as a unitary braze preform comprising an insulator-ferrule portion and a channel portion, the channel portion received in the recess contacting the recess bottom and extending to and contacting the ground pin and the ferrule side wall thereby providing a direct electrical path from the ground pin to the ferrule.

27. The method of claim 24 including providing the ferrule with a bevel where the second braze seals between the ferrule and the insulator.

28. The method of claim 24 including positioning the third end of the ground pin between the first side of the insulator and the recess bottom.

29. The method of claim 24 including positioning the first insulator side spaced above the first ferrule side.

30. The method of claim 24 including providing the first and second braze material being the same or different.

31. The method of claim 24 including providing the first and second braze materials of gold or a gold alloy.

32. The method of claim 24 including coating the first and second braze materials with a pinhole free layer of a biocompatible/biostable material.

33. The method of claim 32 including selecting the biocompatible/biostable material from the group consisting of gold, gold alloys, niobium, carbon, carbon nitride, platinum, titanium, titanium nitrides, titanium carbide, palladium, iridium, iridium oxide, tantalum, tantalum oxide, ruthenium, ruthenium oxide, alumina, zirconium, parylene, silicone, fluoropolymers, and mixtures thereof.

34. The method of claim 24 including positioning a filter capacitor in electrical communication with the at least one lead wire and the at least one ground pin, the filter capacitor shunting electromagnetic interference from the lead wire to the ground pin in electrical communication with the ferrule along the second braze.

35. The method of claim 34 including providing more than one lead wire and providing a corresponding number of capacitors in electrical communication with the lead wires and the at least one ground pin in electrical communication with the ferrule.

* * * * *